United States Patent
Schröder

(10) Patent No.: US 7,777,084 B2
(45) Date of Patent: Aug. 17, 2010

(54) CYCLOPROPANATION PROCESS

(75) Inventor: Fridtjof Schröder, Hettlingen (CH)

(73) Assignee: Givaudan SA, Vernier (CH)

( * ) Notice: Subject to any disclaimer, the term of this patent is extended or adjusted under 35 U.S.C. 154(b) by 535 days.

(21) Appl. No.: 11/722,121

(22) PCT Filed: Dec. 20, 2005

(86) PCT No.: PCT/CH2005/000763

§ 371 (c)(1),
(2), (4) Date: Oct. 16, 2007

(87) PCT Pub. No.: WO2006/066436

PCT Pub. Date: Jun. 29, 2006

(65) Prior Publication Data

US 2008/0275256 A1  Nov. 6, 2008

(30) Foreign Application Priority Data

Dec. 24, 2004 (GB) ................................ 0428294.3
Aug. 30, 2005 (GB) ................................ 0517584.9

(51) Int. Cl.
C07C 43/02 (2006.01)
C07C 27/10 (2006.01)
C07C 315/00 (2006.01)
C07D 313/00 (2006.01)

(52) U.S. Cl. .................. 568/838; 568/700; 568/631; 568/27; 549/269

(58) Field of Classification Search .............. 549/269; 568/838, 700, 631, 27
See application file for complete search history.

(56) References Cited

FOREIGN PATENT DOCUMENTS

EP 0801049 A1 10/1997

OTHER PUBLICATIONS

Frederich et al. Journal of Organic Chemistry, 56, 1991, pp. 2202-2205.*
Keji Maruoka et al., Trialkylaluminium-Alkylidene Iodie. A Powerful Cyclopropanation Agent with Unique Selectivity, 1985, vol. 50, pp. 4412-4414; J. Org. Chem.
International Search Report dated Feb. 23, 2006 for Application PCT/CH2005/000763.
Written Opinion of the International Searching Authority for Application PCT/CH2005/000763.
Edwin C. Friedrich; Regioselectivity and Solvent Effects in Cyclopropanation of Alkadienes, 1991, vol. 56, pp. 2202-2205; J. Org.Chem.

* cited by examiner

*Primary Examiner*—D. Margaret Seaman
*Assistant Examiner*—Nizal S Chandrakumar
(74) *Attorney, Agent, or Firm*—Norris McLaughlin & Marcus, PA

(57) ABSTRACT

A process for the cyclopropanation of a substituted alkene, comprising the reaction of the alkene with a carbenoide, generated from dibromomethane and a tri-$(C_2-C_8)$-alkyl aluminium compound, in the presence of a catalytic amount of a metal compound selected from the group consisting of Lewis acids, metallocenes and metal carbonyl complexes. The process advantageously uses transition metal compounds as catalysts and the dibromomethane can be recovered.

The process is especially useful for the preparation of ingredients for the flavour and fragrance industry.

15 Claims, No Drawings

CYCLOPROPANATION PROCESS

This is an application filed under 35 USC 371 of PCT/CH2005/000763.

This invention relates to a process of preparing cyclopropanated compounds.

A common cyclopropanation reaction is the Simmons-Smith reaction (see Simmons, H. E; Cairns, T. L.; Vladuchick, S. A.; Hoiness, C. M. *Org. React.* (*N.Y.*) 1973, 20, 1-131), which utilises diiodomethane and Zn(Cu). The reaction takes place via the formation of a carbenoide, that is an intermediate of the type M-$CH_2$—X (M=metal, X=halide), which is generated and consumed during a cyclopropanation reaction. Modifications of this reaction have been introduced by Furukawa (Furukawa, J.; Kawabata, N.; Nishimura, J. *Tetrahedron* 1968, 24, 53-58) and later on by Friedrich et al., who replaced diiodomethane by dibromomethane.

The latter carbenoide precursor is not only less expensive, but it also avoids undesirable iodine and iodide wastes. The use of dibromomethane, however, has the disadvantage that it is less reactive than diiodomethane in this reaction. In order to activate the zinc-copper couple for carbenoide formation, it is necessary to use ultrasound (Friedrich, E. C.; Domek, J. M.; Pong, R. Y. *J. Org. Chem.* 1985, 50, 4640-4642) or additives such as copper halides and acetyl halides (Friedrich, E. C.; Niyati-Shirkhodaee, F. *J. Org. Chem.* 1991, 56, 2202-2205). An example of a compound whose preparation utilizes the latter method is

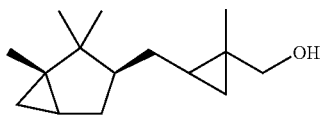

a molecule that has been commercialized successfully as a fragrance component (see EP 0 801 049). A remaining disadvantage of this method, however, is the generation of environmentally-unfriendly zinc- and copper-based wastes.

One theoretical possibility of circumventing these disadvantages is the combination of dibromomethane and a trialkyl aluminum compound. However, this was hitherto not regarded as a viable option. For example, in his paper in *J. Org. Chem.* 1991, 56, 2202-2205, Friedrich states that " . . . the use of $CH_2Br_2$ was examined only (for cyclopropanation) when the Zn/Cu procedure was employed because, with $ZnEt_2$ or $AlEt_3$, dibromomethane has not been reported to react." The theoretical possibility was mentioned in EP 0 801 049, but no teaching on how to achieve it was supplied.

It has now been found that it is possible to utilise dibromomethane and a trialkyl aluminum compound efficiently in a cyclopropanation reaction, if certain metal compounds are added in catalytic amounts.

The invention therefore provides a process for the cyclopropanation of a substituted alkene, comprising the reaction of the alkene with a carbenoide, generated from dibromomethane and a tri-($C_2$-$C_8$)-alkyl aluminium compound in the presence of a catalytic amount of a metal compound selected from the group consisting of Lewis acids other than tri-($C_2$-$C_8$)-alkyl aluminium compounds, metallocenes and metal carbonyl complexes.

By "catalytic amount" is meant an amount of less than one molar equivalent of metal compound with more than one molar equivalent of reactant with the result that more than one molar equivalent of product is obtained.

This method not only gives good yields of the product but is also free from the generation of zinc- and copper-containing residues. The advantage gained by the metal compounds is that the reaction rate of the cyclopropanation reaction is enhanced, thus allowing the use of less dibromomethane and trialkyl aluminum as well as a significantly decreased reaction temperatures.

The $C_2$-$C_8$ alkyl moieties may include alkanes, substituted alkanes, cycloalkanes and substituted cycloalkanes. The ($C_2$-$C_8$) alkyl aluminium compound is preferably triisobutyl aluminium (TIBA).

The method is applicable to electron-rich alkenes. Examples of such alkenes include mono-, di-, tri- or tetra-substituted alkenes. The substituents may be selected from saturated and unsaturated alkyl and aryl groups, which themselves may be substituted with functional groups, such as (but not limited to) acids, esters, alcohols, ethers, allyl alcohols, allyl ethers, amines, allyl amines, imines, alkenes, aldehydes, cyclopropanes and ketones. Alkenes with which the invention works especially well are alkenes bearing at least three substituents including alkenes embedded in ring structures with ring sizes of 3 to 20 carbon- or hetero-atoms, which rings themselves can be substituted, for example, with the same substituents as hereinabove described.

Examples of alkenes that undergo the cyclopropanation reaction of this invention, including combinations of reactive alkenes and unreactive alkenes in the same molecule, include those with the following structures:

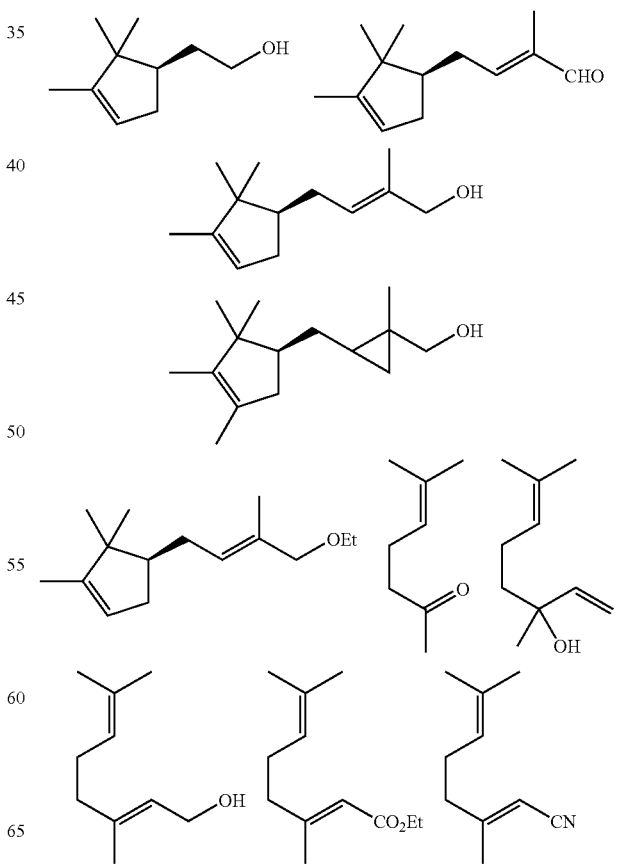

-continued

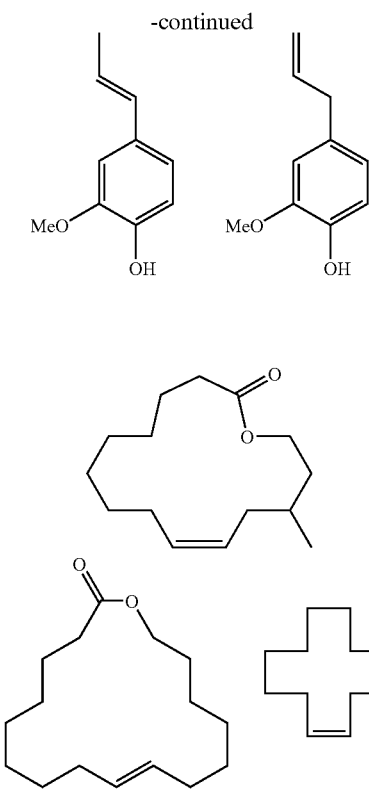

The alkenes may also include in the same molecule alkene moieties that are not electron-rich or alkenes that contain functional groups in their allylic position, which undergo complex formation with the alkyl aluminium compound, e.g.

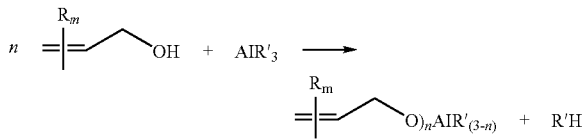

thus shielding these alkenes sterically against cyclopropanation. Examples of these unreactive alkenes are allylic alcohols, allylic amines, as well as electron-deficient alkenes such as conjugated carbonyl compounds, conjugated nitriles, conjugated imines and conjugated oximes. If these unreactive alkenes are combined in the same molecule with electron-rich reactive ones, only the latter will undergo cyclopropanation, with high chemoselectivity.

The metal compounds whose presence is essential to the working of the invention are selected from the group consisting of metallocenes, metal carbonyl complexes and Lewis acids other than tri-$(C_2-C_8)$-alkyl aluminium compounds. One or more of these metal compounds can be used. Although tri-$(C_2-C_8)$-alkyl aluminium compounds are themselves weak Lewis acids, it has been found that they alone do not give the benefits of the invention, and when Lewis acids are desired as the metal compounds, Lewis acids other than these tri-$(C_2-C_8)$-alkyl aluminium compounds must be added.

The rate enhancement brought about by the use of these metal compounds ranges from slight to very significant. Examples of efficient Lewis acids include $FeCl_2$ and $FeCl_3$, which are preferably used at a concentration of 0.01-30%, preferably 1-10%, with respect to the alkene to be cyclopropanated (the starting material). Examples of efficient metallocenes are those with at least one cyclopentadienyl-ligand, e.g. cyclopentadienyltitanium trichloride $CpTiCl_3$ or cyclopentadienyliron dicarbonyl dimer $[CpFe(CO)_2]_2$, which are used at the concentrations hereinabove described. An example of a metal carbonyl complex is iron pentacarbonyl $Fe(CO)_5$. The addition has the advantage of allowing the reaction to be carried out in less dibromomethane, typically 20 molar equivalents instead of 30 eq, and at lower temperatures, thus increasing the margin of safety, because above 85° C. an exothermic decomposition of the reaction mass is possible. For example, with $FeCl_3$, this reaction proceeds as follows:

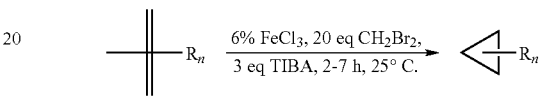

In a preferred embodiment, the excess dibromomethane is recovered. Although not essential to the working of the invention, such a recovery reduces costs and makes the process more industrially viable. The recovery is carried out by the steps of:

(i) adding the reaction mixture to aqueous base at a temperature from −10°-0° C.;

(ii) warming slowly the resulting two-phase mixture to room temperature;

(iii) separating the phases;

(iv) adding isopropanol to the organic phase; and (v) drying azeotropically and evaporating the dibromomethane under reduced pressure.

In a typical example, using the preferred TIBA, recovery may be achieved by the following steps:

(i) The reaction mixture is added to aqueous base (preferably 25% NaOH) at a temperature of from −10°-0° C. Isobutane is cleaved from the isobutyl aluminium reagent and remains liquefied in the target vessel.

(ii) The resulting two-phase mixture is slowly and under stirring warmed to room temperature. This causes the release of gaseous isobutane, which is collected in a cooling device;

(iii) after phase separation and addition of isopropanol to the organic phase, the organic phase is dried azeotropically and the excess dibromomethane is evaporated under reduced pressure and finally purified by distillation.

The process described in this invention permits the cyclopropanation of electron-rich olefins in a cheap and efficient manner. The aluminium- and iron-containing wastes are environmentally of relatively low concern, the solvent dibromomethane can be recycled, and the collected isobutane can be used for other purposes or can be burned.

The process has many uses, including the relatively easy and inexpensive manufacture of flavour and fragrance ingredients.

The invention is now further described with reference to the following non-limiting examples.

EXAMPLE 1

Cyclopropanation of Campholene Alcohol: trans-2-(1,2,2-trimethyl-bicyclo[3.1.0]hex-3-yl)-ethanol

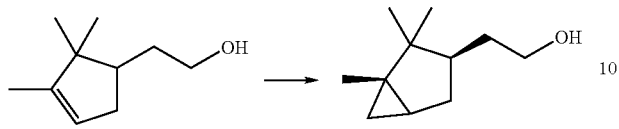

Campholene alcohol (EP 0 116 903) (8 g, 50 mmol) in dibromomethane (72 ml) is treated under cooling (10°-20° C.) with neat TIBA (6.5 ml, 25 mmol) via syringe. After 15 min stirring anhydrous FeCl₃ (0.5 g, 3 mmol) is added followed by neat TIBA (39 ml, 0.15 mol). The mixture is stirred for 3 h at 25° C., then cooled to −10°-0° C. and pumped via double-needle on to 25% NaOH at −10°-0° C. Under stirring the biphasic mixture is slowly warmed to room temperature. The phases are separated. The organic phase is washed with 4% oxalic acid, then with conc. NaHCO₃ until pH ~8, dried over MgSO₄ and filtered. After evaporation of the solvents under reduced pressure, the oily residue is purified by bulb-to-bulb-distillation (bp 108° C./0.1 Torr), giving 7.3 g (85%) of a colorless oil. Odour: Camphoraceous, oily. ¹H-NMR (CDCl₃, 400 MHz): 3.65 (ddd, 1H), 3.5 (ddd, 1H), 1.7 (dd, 1H), 1.6 (m, 1H), 1.4 (m, 1H), 1.3 (m, 1H), 1.2 (m, 1H), 1.05 (s, 3H), 1.0 (m, 1H), 0.89 (s, 1H), 0.78 (s, 1H), 0.45 (dd, 1H), 0.02 (dd, 1H) ppm. ¹³C-NMR (CDCl₃, 400 MHz): 62.6 (t), 41.4 (s), 40.6 (d), 33.4 (t), 32.3 (t), 31.2 (s), 22.8 (d), 22.7 (q), 19.8 (q), 17.4 (q), 13.9 (t) ppm. Relative configuration determined by HSQC, COSYDQF, HMBC, NOESY. GC/MS: 168 (1%, [M]⁺), 153 (60%, [M-CH₃]⁺), 109 (90%), 81 (80%), 55 (83%), 41 (100%). IR (film): 3325 (m), 2951 (s), 2868 (m), 1464 (m), 1451 (m), 1363 (m), 1056 (m), 1034 (m).

EXAMPLE 2 trans-[1-Methyl-2-(1,2,2,5-tetramethyl-bicyclo[3.1.0]hex-3-ylmethyl)-cyclopropyl]methanol

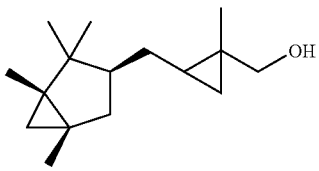

(i) Preparation of the Precursor: trans-[1-Methyl-2-(2,2,3,4-tetramethyl-cyclopent-3-enylmethyl)-cyclopropyl]methanol

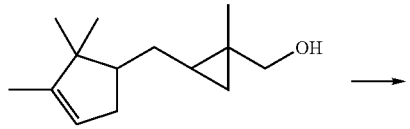

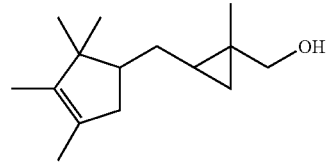

trans-[1-Methyl-2-(2,2,3-trimethyl-cyclopent-3-enylmethyl)-cyclopropyl]-methanol (dr=1:1) (Bajgrowicz, J. A.; Frank, I.; Frater, G.; Hennig, M., *Helv. Chim. Acta* 1998, 81, 1349-1358) (10 g, 48 mmol), dihydropyrane (4.3 g, 51 mmol) and a few drops of conc. HCl (50 mg) are stirred for 4 h at 25° C. After addition of methyl tert-butyl ether the organic phase is washed with conc. NaHCO₃ and conc. NaCl until pH=7. Drying over MgSO₄, filtration and evaporation gives 14 g (93%) of the crude THP-ether as an oil (4 isomers, 93% purity and M=292 according to GC/MS), which is subjected to the next epoxidation step without further purification.

The thus-obtained crude THP-ether (11.7 g, 40 mmol) is dissolved in dichloromethane (20 ml). After addition of water-free Na₂CO₃ (5.9 g, 56 mmol) the mixture is heated to 42° C., where 40% peracetic acid (10 ml, 56 mmol) are added over 2 h. The reaction is stirred for another 1 h at this temperature. Water (50 ml) is carefully added and the phases are separated. The water phase is extracted with dichloromethane. The organic phase is washed with 10% NaOH and water until pH=7. Drying over MgSO₄, filtration and evaporation gives 12.3 g (87%) of the crude THP-protected epoxide as an oil (4 isomers, 87% purity and M=308 according to GC/MS), which is subjected without further purification to the next Grignard addition/elimination step.

The thus-obtained THP-protected epoxide (8.6 g, 28 mmol) is treated with 3M methyl magnesiumchloride in tetrahydrofurane (94 ml, 0.28 mol). After 3 days at 70° C. the solution is poured upon NH₄Cl at 0° C. Methyl tert-butyl ether extraction and washing of the organic phase with water until pH=7, MgSO₄-drying, filtration and evaporation gives 10 g of an orange oil, which is treated with methanol (10 g) and para-toluenesulfonic acid (0.1 g). After 16 h at 25° C. the methanol is evaporated, conc. NaHCO₃ and methyl tert-butyl ether are added and the phases are separated. MgSO₄-drying, filtration and evaporation of the organic phase gives 7 g of an orange oil, which is purified by flash chromatography (hexane/methyl tert-butyl ether) over silicagel giving after evaporation of the solvents and Kugelrohr distillation 1.9 g (31%) of trans-[1-Methyl-2-(2,2,3,4-tetramethyl-cyclopent-3-enylmethyl)-cyclopropyl]-methanol as a colorless oil (dr=1:1, 84% GC-purity). Odour: Sandalwood, substantive. ¹H-NMR (CDCl₃, 400 MHz): 3.35 (2H), 2.3 (m, 1H), 1.95 (m, 1H), 1.75 (m, 1H), 1.6 (s, 3H), 1.5 (s, 3H), 1.5-1.2 (5H), 1.15 (s, 3H), 0.95 (s, 3H), 0.7 (d, 3H), 0.65 (m, 1H), 0.5 (m, 1H), 0 (2 m, 1H) ppm. ¹³C-NMR (CDCl₃, 400 MHz): 139.04 and 139.03 (2 s), 128.6 and 128.5 (2 s), 72.7 and 72.6 (2 t), 49.7 and 49.3 (2 d), 48.0 and 47.8 (2 s), 41.62 and 41.59 (2 t), 29.1 and 28.6 (2 t), 26.2 and 26.1 (2 q), 22.7 and 21.8 (2 s), 21.3 and 21.0 (2 d), 19.7 and 19.6 (2 q), 17.0 and 16.5 (2 t), 15.7 (q), 15.1 (q), 14.2 (q), 9.45 and 9.43 (2 q). GC/MS: 222 (3%, [M]⁺), 150 (22), 135 (35%), 121 (55%), 107 (100%). IR (film): 3327 (m), 2951 (s), 2851 (s), 2915 (m), 2861 (m), 1445 (m), 1382 (m), 1359 (m), 1027 (s), 881 (w).

(ii) Cyclopropanation Reaction: Preparation of trans-[1-Methyl-2-(1,2,2,5-tetramethyl-bicyclo[3.1.0]hex-3-ylmethyl)cyclopropyl]methanol

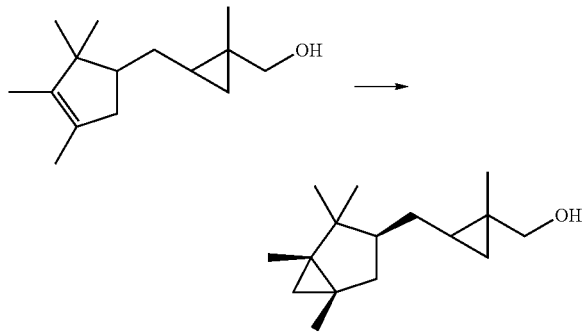

Prepared as described in example 1 from trans-[1-Methyl-2-(2,2,3,4-tetramethyl-cyclopent-3-enylmethyl)-cyclopropyl]-methanol (0.5 g, 2.2 mmol), dibromomethane (3 ml, 45 mmol), TIBA (2 ml, 8 mmol) and FeCl₃ (22 mg, 0.13 mmol) giving after bulb to bulb-distillation (bp 128° C./0.2 Torr) 0.46 g (85%) of a colorless oil (dr=1:1, 91% GC-purity). Odour: Sandalwood, substantive. $^1$H-NMR (CDCl$_3$, 400 MHz): 3.3 (m, 2H), 1.9 (m, 1H), 1.5 (s, 1H, OH), 1.3-1.1 (3H), 1.1 (2 s, 3H), 1.0 (s, 1H), 0.95 (s, 1H), 0.89 (s, 1H), 1.0-0.8 (2H), 0.75 (d, 3H), 0.6-0.4 (3H), 0.0 and −0.1 (2 t, 1H), −0.3 (d, 1H) ppm. $^{13}$C-NMR (CDCl$_3$, 400 MHz): 72.7 and 72.6 (2 t), 44.8 and 44.4 (2 d), 42.6 and 42.5 (2 s), 39.94 and 39.89 (2 t), 34.9 and 34.8 (2 s), 29.4 and 28.8 (2 t), 26.2 and 26.1 (2 s), 23.1 and 23.0 (2 q), 22.8 and 21.9 (2 s), 21.6 and 21.2 (2 d), 19.8 and 19.7 (2 t), 19.6 and 19.5 (2 q), 18.4 (2 q), 17.1 and 16.5 (2 t), 15.7 and 15.1 (2 q), 14.02 and 14.01 (2 q) ppm. GC/MS: 236 (0.2%, [M]$^+$), 218 (1%), 203 (5%), 175 (5%), 164 (15%), 149 (30%), 135 (85%), 121 (80%), 107 (60%), 95 (80%), 82 (80%), 55 (85%), 41 (100%). IR (film): 3323 (m), 3064 (w), 2866 (s), 1452 (s), 1381 (m), 1362 (m), 1028 (s), 1012 (s), 880 (w).

EXAMPLE 3

Distal-Selective Cyclopropanation of Nor-Radjanol: trans-2-Methyl-4-(1,2,2-trimethyl-bicyclo-[3.1.0]hex-3-yl)but-2-en-1-ol

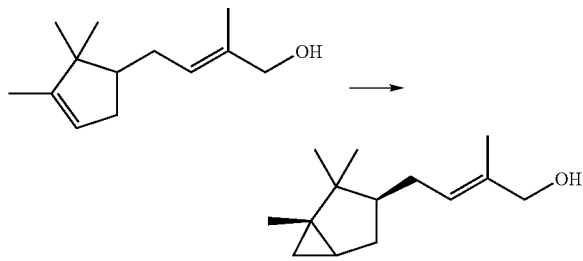

To Nor-Radjanol (Bajgrowicz, J. A.; Frank, I.; Frater, G.; Hennig, M., *Helv. Chim. Acta* 1998, 81, 1349-1358) (194 g, 1 mol) in dibromomethane (1.4 l, 20 mol) neat TIBA (100 g, 0.5mol) is added under cooling (10°-20° C.) via double-needle.

After 15 min anhydrous FeCl₃ (22 mg, 0.13 mmol) is added in one portion followed by TIBA (620 g, 3.1 mol) via double needle. The mixture is stirred for 4.5 h at 25° C., then cooled to −10°-0° C. and pumped via double needle on to cooled (−10-0° C.) 25% NaOH. Under stirring (Caution!) the biphasic mixture is slowly warmed to room temperature. The evolving isobutane is collected in a cooling trap at −78° C. The phases are separated. The organic phase is washed with 4% oxalic acid, then with conc. NaHCO₃ until pH ~8. Isopropanol (110 g, 1.8 mol) is added to the organic phase and the water is removed azeotropically under reduced pressure. Then, the remaining water-free dibromomethane is removed under reduced pressure, followed by distillation of the residue (bp 160° C./0.1 Torr) giving 190 g (93%) of a colorless oil (86% GC-purity, 2% Nor-Radjanol 7% bis-cyclopropanated byproduct), whose analytical data (NMR, MS, IR, odour) are consistent with the ones described in the literature (Bajgrowicz, J. A.; Frank, I.; Frater, G.; Hennig, M., *Helv. Chim. Acta* 1998, 81, 1349-1358).

EXAMPLE 4

This is a comparative example that uses no metal compound.

trans-2-Methyl-4-(1,2,2-trimethyl-bicyclo-[3.1.0]hex-3-yl)but-2-en-1-ol from Nor-Radjaldehyde Via Solvent-Free DIBAH Reduction

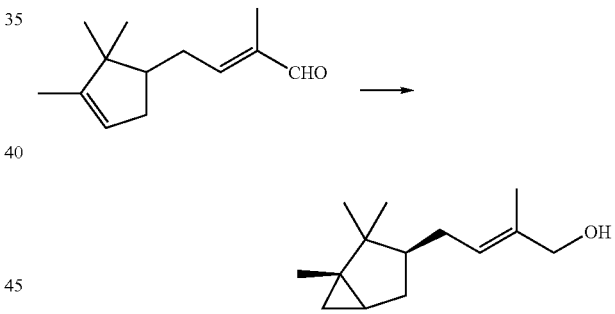

To Nor-Radjaldehyde (U.S. Pat. No. 4,052,341) (192 g, 1 mol) is added at 0° C. and stirring neat DIBAH (179 ml, 1 mol) via double needle. The solution is stirred for 30 min at 25° C. Dibromomethane (2.1 l, 30 mol) is added and the solution heated to 60° C., where neat TIBA (595 g, 3 mol) is added over 2 h via double-needle. The reaction temperature is maintained by slight external cooling at 65-75° C. for another 2-4 h, until complete conversion is detected by GC. Work-up, as described in example 3, gives 227 g (>91%) of crude product as a slightly yellow oil, whose analytical data (NMR, IR, MS, odour) are consistent with the ones described for this compound in the literature (Bajgrowicz, J. A.; Frank, I.; Frater, G.; Hennig, M., *Helv. Chim. Acta* 1998, 81, 1349-1358).

In comparison with Example 1, it can be seen that, without FeCl₃, more TIBA and dibromomethane are required and that a higher reaction temperature is necessary. The use of FeCl₃ allows a better, more economic process.

EXAMPLE 5

Distal-Selective Cyclopropanation of Linalool: 5-(2,2-Dimethyl-cyclopropyl)-3-methyl-pent-1-en-3-ol

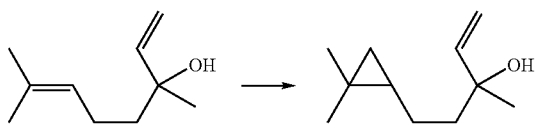

Prepared as described in example 1 from Linalool (31 g, 0.2 mol), dibromomethane (280 ml), neat TIBA (140 g, 0.7 mol) and anhydrous $FeCl_3$ (2 g, 60 mmol). Work-up after 6 h at 25° C. and distillation (bp 55° C./0.05 Torr) gives 22.5 g (67%) of the cyclopropanation product as colorless oil, whose analytical data are consistent with the ones described in WO 01/006853. Odour: citrus, green, cool, metal.

EXAMPLE 6

Distal-Selective Cyclopropanation of Geraniol: E-5-(2,2-Dimethyl-cyclopropyl)-3-methyl-pent-2-en-1-ol

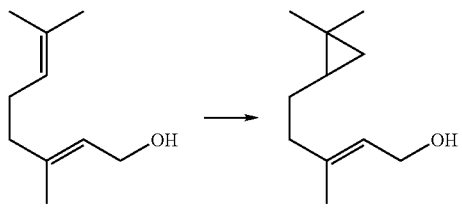

Prepared as described in example 3 from E-Geraniol (154 g, 1 mol), dibromomethane (1.4 l, 20 mol), neat TIBA (700 g, 3.5 mol) and anhydrous $FeCl_3$ (10 g, 60 mmol). Work-up after 7 h at 25° C. gives 175 g of the crude cyclopropanation product (81% GC-purity) as yellowish oil, which is instable to distillation ($H_2O$ elimination) and on prolonged standing. Odour: weak Geraniol. $^1$H-NMR ($CDCl_3$, 400 MHz): 5.4 (t, 1H), 4.15 (d, 2H), 2.1 (dd, 2H), 1.7 (s, 1H), 1.6 (s, 3H), 1.4 (m, 2H), 1.03 (s, 3H), 1.02 (s, 3H), 0.4 (1H), 0.35 (dd, 1H), −0.15 (dd, 1H) ppm. $^{13}$C-NMR ($CDCl_3$, 400 MHz): 140.0 (s), 123.2 (d), 59.3 (t), 40.0 (t), 28.2 (t), 27.6 (q), 24.3 (d), 19.9 (q), 19.6 (t), 16.3 (q), 15.4 (s) ppm. GC/MS: 153 (2%, [M-15]$^+$), 150 (2%, [M-$H_2O$]$^+$), 137 (18%), 107 (25%), 82 (45%), 67 (55%), 55 (100%).

EXAMPLE 7

Reduction/Cyclopropanation of 6-Methyl-hept-5-en-2-one: 4-(2,2-Dimethyl-cyclopropyl)-butan-2-ol

$FeCl_3$ (0.5 g, 3 mmol) is added under stirring to 6-Methyl-hept-5-en-2-one (6.3 g, 50 mmol) in dibromomethane (70 ml, 1 mol) at 10°-20° C., followed by slow addition of neat TIBA (38 ml, 0.15 mol) at this temperature. The mixture is stirred for 7 h at 25° C., then poured carefully on to 25% NaOH at −10°-0° C. Work-up as described in example 1 and distillation (bp 50° C./0.07 Torr) gives 4.8 g (67%) of a colorless oil (80% GC-purity, dr ~1:1). The analytical data (NMR, MS, IR) are consistent with the ones described in the literature (Perraud, R; Arnaud, P. Bull. Chem. Soc. Chim. Fr. 1968, 1540-1542).

EXAMPLE 8

Cyclopropanation of Isoeugenol: trans-2-Methoxy-4-(2-methyl-cyclopropyl)phenol

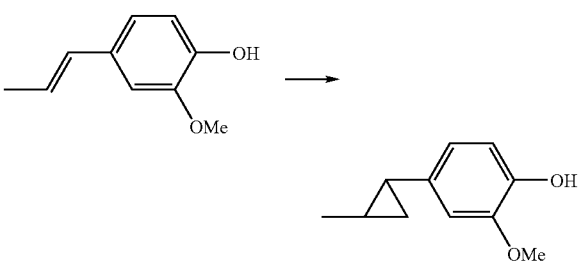

Prepared as described in example 3 from Isoeugenol (100 g, 0.61 mol), dibromomethane (850 ml, 12.2 mol), neat TIBA (422 g, 2.15 mol) and anhydrous $FeCl_3$ (6 g, 37 mmol). After 7 h at 25° C. (conversion 44:56) the mixture is cooled to −10°-0° C. and pumped via double needle on to 2 M HCl cooled to −10°-0° C. Under stirring (Caution!) the biphasic mixture is slowly warmed to room temperature. The organic phase is separated and washed with 5% citric acid and water until pH=7. Drying with $MgSO_4$, filtration and evaporation of the solvent, followed by distillation (bp 65° C./0.03 Torr) gives 50.1 g (46%) of the cyclopropanation product as colorless oil (93% GC-purity). The analytical data (NMR, MS, IR, odour) are consistent with the ones described for this compound in EP 1 269 982.

EXAMPLE 9

Cyclopropanation of Eugenol: 4-Cyclopropylmethyl-2-methoxy-phenol

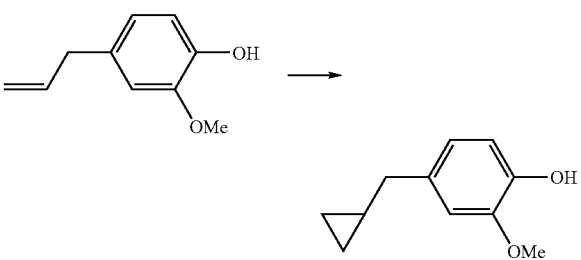

Prepared as described in example 8 from Eugenol (50 g, 0.3 mol), dibromomethane (425 ml, 6.1 mol), neat TIBA (212 g, 1.06 mol) and anhydrous $FeCl_3$ (3 g, 18 mmol). The mixture is worked-up after 20 h at 25° C. (57:43 conversion) as described in example 8. Distillation at 75° C./0.03 Torr separates the substrate (bp 50° C., 0.03 Torr) from the cyclopropanation product (bp 75° C., 0.03 Torr) giving 21 g (41%) of the latter compound as colorless oil, whose analytical data (NMR, MS, IR, odour) are consistent with the ones described in EP 1 269 982.

EXAMPLE 10

Distal-Selective Cyclopropanation of Geranic Acid Ethyl Ester: E-5-(2,2-Dimethyl-cyclopropyl)-3-methyl-pent-2-enoic acid ethyl ester

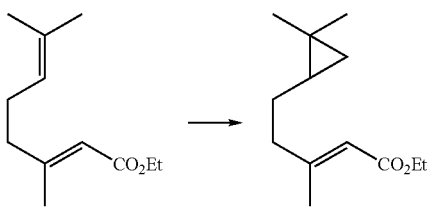

Prepared as described in example 7 from anhydrous FeCl$_3$ (0.1 g, 0.7 mmol), Geranic acid ethyl ester (2.2 g, 11 mmol), dibromomethane (31 ml, 0.44 mol) and neat TIBA (17 ml, 66 mmol). Work-up after 6 h at 25° C., as described in example 1, and Kugelrohr distillation (bp 92° C./0.2 Torr) gives 1.2 g (52%) of a colorless oil. Odour: fruity, pear. $^1$H-NMR (CDCl$_3$, 400 MHz): 5.7 (s, 1H), 4.15 (q, 2H), 2.2 (t, 1H), 2.18 (s, 3H), 1.5 (1H), 1.3 (t, 3H), 1.1 (s, 3H), 1.0 (s, 3H), 0.9 (2H), 0.45 (1H), 0.4 (1H), −0.1 (1H) ppm. $^{13}$C-NMR (CDCl$_3$, 400 MHz): 166.7 (s), 160.1 (s), 115.4 (d), 59.2 (t), 41.4 (t), 28.0 (t), 27.4 (q), 24.1 (d), 19.8 (q), 19.6 (t), 18.7 (q), 15.4 (s), 14.2 (q) ppm. GC/MS: 210 (0.1%, M$^+$), 195 (4%, [M 15]$^+$), 153 (10%), 136 (35%), 82 (45%), 55 (100%). IR (film): 2925 (m), 2869 (m), 1719 (s), 1648 (m), 1453 (m), 1366 (m), 1219 (m), 1147 (s), 1042 (m), 970 (w), 859 (w).

EXAMPLE 11

Cyclopropanation of E/Z-Geranitrile: E/Z-5-(2,2-dimethyl-cyclopropyl)-3-methyl-pent-2-enenitrile

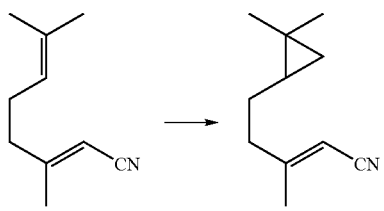

Prepared as described in example 7 but in 2 cycles from E/Z-Geranitrile (dr=1:1) (77 g, 0.52 mol), dibromomethane (2×720 ml, 10.3 mol), neat TIBA (2×358 g, 1.8 mol) and anhydrous FeCl$_3$ (2×5 g, 30 mmol). Work-up after 17 h at 25° C. (per cycle), as described in example 1, and distillation (bp 95° C./0.06 Torr) (after the 2$^{nd}$ cycle) gives 50 g (59%) of the cyclopropanation product (71% GC-purity, 8% aldehyde, 11% alcohol, dr=1:1) as colorless oil. $^1$H-NMR (CDCl$_3$, 400 MHz): 5.1 (1H), 2.5 (m, 1H), 2.25 (m, 1H), 2.05 (s, 1.5H), 1.9 (s, 1.5H), 1.6-1.3 (2H), 1.05 (6H), 0.45 (2H), −0.1 (1H) ppm. $^{13}$C-NMR (CDCl$_3$, 400 MHz): 165.43 and 165.4 (2 s), 117.2 and 117.0 (2 s), 95.6 and 95.0 (2 d), 39.1 and 36.7 (2 t), 27.6 and 27.5 (2 t), 27.39 and 27.37 (2 q), 28.9 and 23.8 (2 d), 22.9 and 21.0 (2 q), 19.9 and 19.8 (2 q), 15.6 and 15.5 (2 s) ppm. GC/MS: 162 (20%), 148 (1%, [M-15]$^+$), 94 (20%), 81 (55%), 55 (100%). IR (film): 2952 (s), 2867 (m), 2218 (w), 1676 (w), 1632 (w), 1454 (m), 1377 (m), 1365 (m), 1120 (w), 1020 (m), 866 (w), 801 (w). Odour: Hesperidic, powerful, fresh, geranitrile.

EXAMPLE 12

Cyclopropanation of E-Ambrettolide: trans-8-oxa-bicyclo[15.1.0]octadecan-9-one

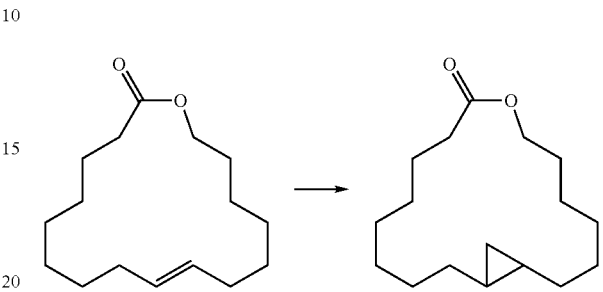

Prepared as described in example 7 but in 2 cycles from E-Ambrettolide (20 g, 80 mmol), dibromomethane (2×110 ml, 1.6 mol), neat TIBA (2×47 g, 0.24 mol) and anhydrous FeCl$_3$ (2×0.8 g, 5 mmol). Work-up after 6 h at 25° C. (per cycle), as described in example 1, and distillation (bp 130° C./0.04 Torr) (after the 2$^{nd}$ cycle) gives 6.6 g (30%) of the cyclopropanation product (97% GC-purity) as colorless oil. $^1$H-NMR (CDCl$_3$, 400 MHz): 4.2 (m, 1H), 2.35 (m, 2H), 1.85 (1H), 1.7-1.6 (5H), 1.5-1.2 (14H), 0.8 (m, 1H), 0.55 (m, 1H), 0.45 (m, 1H), 0.35 (1H), 0.2 (2H) ppm. $^{13}$C-NMR (CDCl$_3$, 400 MHz): 173.9 (s), 63.9 (t), 34.8 (t), 33.9 (t), 33.5 (t), 29.8 (t), 29.5 (t), 29.5 (t), 29.1 (t), 28.6 (t), 28.31 (t), 28.29 (t), 26.4 (t), 25.6 (t), 18.63 (d), 18.56 (d), 11.9 (t) ppm. GC/MS: 266 (1%, M$^+$), 248 (1%, [M-18]$^+$), 123 (10%), 109 (22%), 96 (50%), 82 (63%), 67 (75%), 55 (100%). IR (film): 2921 (s), 2851 (m), 1733 (s), 1460 (m), 1347 (w), 1237 (m), 1161 (m), 1113 (w), 1057 (w), 1022 (w), 720 (w).

EXAMPLE 13

Cyclopropanation of Nirvanolide™: cis-3-Methyl-6-oxa-bicyclo[13.1.0]hexadecan-7-one.

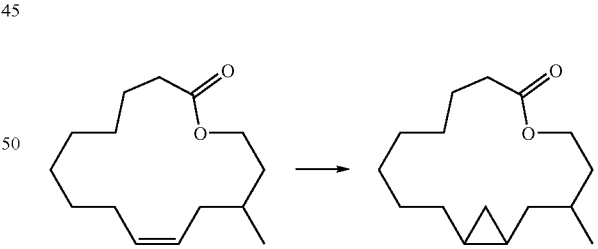

Prepared as described in example 7 from Nirvanolide (Frater, G.; Helmlinger, D.; Mueller, U. Givaudan-Roure (International) S.A., 1999, EP 908455) (20 g, 84 mmol), dibromomethane (235 ml, 3.35 mol), neat TIBA (100 g, 0.5 mol) and anhydrous FeCl$_3$ (0.8 g, 5 mmol). Work-up after 5 h at 25° C., as described in example 1, and distillation (bp 100° C./0.03 Torr) gives 8 g (38%) of the cyclopropanation product as colorless oil. Odour: musky, metal, powdery. 1H-NMR (CDCl$_3$, 400 MHz): 4.2 (m, 2H), 2.3 (m, 2H), 1.7 (1H), 1.7-1.2 (16H), 1.0 (3H), 0.8 (m, 1H), 0.6 (m, 1H), −0.3 (m, 1H) ppm. $^{13}$C-NMR (CDCl$_3$, 400 MHz): 174.0 (s), 62.1 (t), 37.4 (t), 36.3 (t), 34.6 (t), 30.2 (d), 28.6 (t), 27.6 (t), 27.5 (t), 27.1 (t), 26.8 (t), 24.8 (t), 18.4 (q), 16.1 (d), 13.8 (d), 10.9 (t) ppm. GC/MS: 252 (1%, M+), 237 (1%, [M-15]+), 223 (1%), 210 (1%), 195 (1%), 182 (1%), 109 (20%), 95 (35%), 81 (100%). IR (film): 2924 (m), 2855 (m), 1731 (s), 1458 (m), 1378 (w), 1337 (w), 1248 (m), 1151 (m), 1120 (w), 1091 (w), 1060 (m), 1021 (w), 965 (w), 848 (w).

EXAMPLE 14 trans-3-(2-Ethoxymethyl-2-methyl-cyclopropylmethyl)-1,2,2-trimethyl-bicyclo-[3.1.0]hexane

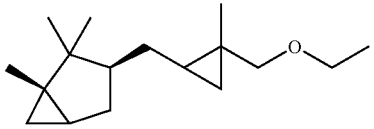

(i) Preparation of the Precursor: E-4-(4-Ethoxy-3-methyl-but-2-enyl)-1,5,5-trimethyl-cyclopentene

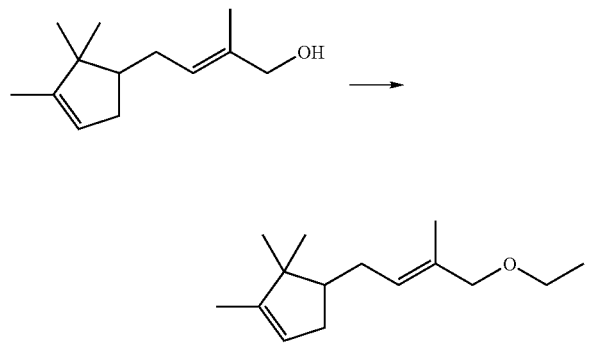

A solution of Nor-Radjanol (Bajgrowicz, J. A.; Frank, I.; Frater, G.; Hennig, M. *Helv. Chim. Acta* 1998, 81, 1349-1358) (60 g, 0.3 mol) and ethyl iodide (73 ml, 0.47 mol) in non-aqueous tetrahydrofuran (400 ml) is cooled to −50° C., where 50% NaH (20 g, 0.42 mol) is added in one portion. The stirred mixture is slowly warmed up to 25° C. and is kept at this temperature under cooling until the exothermy ceases. After dilution with methyl tert-butyl ether, water is added carefully. The organic phase is separated, washed with water until pH=7 and dried over MgSO$_4$. Filtration and evaporation of the solvent under reduced pressure gives 76 g of a residue, which is distilled (bp 65° C./0.03 Torr) giving 61 g (89%) of a colorless oil. Odour: earthy, agrestic, green. $^1$H-NMR (CDCl$_3$, 400 MHz): 5.4 (t, 1H), 5.2 (s, 1H), 3.85 (s, 1H), 3.4 (q, 2H), 2.3 (m, 1H), 2.2 (m, 1H), 2 (m, 1H), 1.8 (2H), 1.65 (s, 3H), 1.6 (s, 3H), 1.2 (t, 3H), 1.0 (s, 3H), 0.8 (s, 3H) ppm. $^{13}$C-NMR (CDCl$_3$, 400 MHz): 148.4 (s), 132.2 (s), 127.5 (d), 121.6 (d), 76.7 (t), 64.6 (t), 50.2 (d), 46.6 (s), 35.5 (t), 28.1 (t), 25.7 (q), 19.6 (q), 15.1 (q), 13.8 (q), 12.5 (q) ppm. GC/MS: 222 (5%, M+), 207 (8%, [M-15]+), 176 (40%, [M-EtOH]+), 161 (100%), 121 (65%), 108 (100%), 93 (95%). IR (film): 2955 (m), 2865 (m), 1444 (m), 1381 (m), 1359 (m), 1090 (s), 1011 (m), 861 (w), 799 (m).

(ii) Cyclopropanation of E-4-(4-Ethoxy-3-methyl-but-2-enyl)-1,5,5-trimethyl-cyclopentene: trans-3-(2-Ethoxymethyl-2-methyl-cyclopropylmethyl)-1,2,2-trimethyl-bicyclo-[3.1.0]hexane

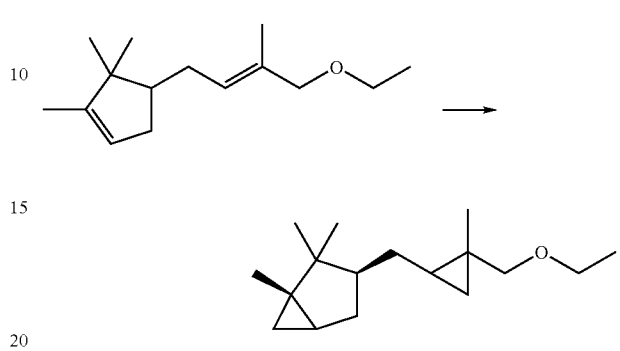

Prepared as described in example 7 from E-4-(4-ethoxy-3-methyl-but-2-enyl)-1,5,5-trimethyl-cyclopentene (1.56 g, 7 mmol), dibromomethane (28 ml, 0.4 mol), neat TIBA (15 ml, 60 mmol) and anhydrous FeCl$_3$ (0.2 g, 1.2 mmol). Work-up after 1.5 h at 25° C., as described in example 1, and Kugelrohr distillation (bp 100° C./0.07 Torr) gives 0.9 g (52%) of the bis-cyclopropanation product as colorless oil (dr=1:1). $^1$H-NMR (CDCl$_3$, 400 MHz): 3.45 (q, 2H), 3.2-3.1 (m, 2H), 1.85 (m, 1H), 1.6-0.8 (6H), 1.2 (t, 3H), 1.1 (2 s, 3H), 1.02 (s, 3H), 0.85 (s, 3H), 0.75 (2 s, 3H), 0.5-0.45 (3H), −0.1-0.0 (2H) ppm. $^{13}$C-NMR (CDCl$_3$, 400 MHz): 79.93 and 79.90 (2 t), 65.8 and 65.8 (2 t), 45.1 and 44.7 (2 d), 41.4 and 41.1 (2 d), 32.5 and 32.4 (2 t), 31.4 and 31.2 (2 s), 29.6 and 28.9 (2 t), 22.9 and 22.8 (2 s), 22.7 and 22.6 (2 d), 21.3 and 21.1 (2 d), 20.3 (s), 19.7 and 19.6 (2 q), 19.6 (q), 19.1 (s), 17.41 and 17.38 (2 q), 16.0 (2 q), 15.5 (2 q), 15.19 and 15.17 (2 q), 13.92 and 13.88 (2 t) ppm. GC/MS: 250 (1%, M+), 235 (2%, [M-15]+), 204 (4%, [M-EtOH]+), 189 (12%), 149 (30%), 121 (60%), 107 (80%), 86 (100%). IR (film): 2952 (m), 2927 (m), 2856 (m), 1451 (m), 1378 (m), 1362 (m), 1297 (m), 1105 (s), 1014 (m), 872 (w), 838 (w).

EXAMPLE 15

Cyclopropanation of Z-Cyclododecene: cis-Bicyclo[10.1.0]tridecane

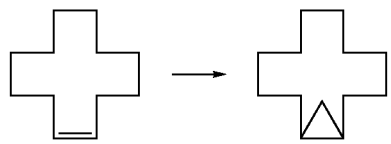

Prepared as described in example 7 from Z-Cyclododecene (E/Z=3:1) (1.66 g, 10 mmol), dibromomethane (14 ml, 0.2 mol), neat TIBA (7.5 ml, 30 mmol) and anhydrous FeCl$_3$ (0.1 g, 0.6 mmol). Work-up after 2 h at 25° C., as described in example 1, and Kugelrohr distillation (bp. 60° C./0.07 Torr) gives 1.5 g (83%) of the cyclopropanation product as colorless oil (cis/trans 3:1), whose analytical data (NMR, MS) are consistent with the ones described in the literature (O'Connor, E. J.; Brandt, S.; Helquist, P.; *J. Am. Chem. Soc.* 1987, 109, 3739-3747).

EXAMPLE 16

[CpFe(CO)$_2$]$_2$-catalyzed cyclopropanation of Nor-Radjanol: trans-2-methyl-4-(1,2,2-trimethyl-bicyclo-[3.1.0]hex-3-yl)but-2-en-1-ol Prepared, as described in example 3, from Nor-Radjanol (1.94 g, 10 mmol), dibromomethane (14 ml, 0.2 mol), neat TIBA (8.8 ml, 35 mmol), and with cyclopentadienyliron dicarbonyl dimer [CpFe(CO)$_2$]$_2$ (100 mg, 0.3 mmol) in place of the FeCl$_3$ of that example. Work-up after 3 h at 25° C., Silicagel filtration and bulb-to-bulb distillation gives 1.9 g (91%) of a colorless oil (85% GC-purity), whose analytical data are consistent with the ones described for the same product obtained from example 3.

EXAMPLE 17

CpTiCl$_3$-Catalyzed Cyclopropanation of Nor-Radjanol: trans-2-methyl-4-(1,2,2-trimethyl-bicyclo-[3.1.0]hex-3-yl)but-2-en-1-ol Prepared, as described in example 3, from Nor-Radjanol (1.94 g, 10 mmol), dibromomethane (14 ml, 0.2 mol), neat TIBA (8.8 ml, 35 mmol), and with cyclopentadienyltitanium trichloride CpTiCl$_3$ (100 mg, 0.3 mmol) in place of the FeCl$_3$ of that example. Work-up after 3 h at 25° C. and bulb-to-bulb distillation gives 1.8 g (85%) of a colorless oil (77% GC-purity), whose analytical data are consistent with the ones described for the same product obtained from example 3.

The invention claimed is:

1. A process for the cyclopropanation of a substituted alkene, comprising the step of:
    reacting said substituted alkene with a carbenoide, generated from dibromomethane and a tri-(C$_2$-C$_8$)-alkyl aluminium compound in the presence of a catalytic amount of a metal compound selected from the group consisting of Lewis acids other than tri-(C$_2$-C$_8$)-alkyl aluminium compounds, metallocenes and metal carbonyl complexes.

2. A process according to claim 1, in which the tri-(C$_2$-C$_8$)-alkyl aluminium is triisobutyl aluminium.

3. A process according to claim 1, in which there is used from 1-5 molar equivalents, of tri-(C$_2$-C$_8$)-alkyl aluminium reagent.

4. A process according to claim 1, in which there is used from 5-100 molar equivalents, of dibromomethane.

5. A process according to claim 1, in which the metal compound is a Lewis acid selected from the group consisting of copper and iron halides.

6. A process according to claim 1, in which the metal compound is a metallocene containing at least one cyclopentadienyl-ligand.

7. A process according to claim 1 in which the metal compound is used at a concentration of 0.01-30%, with respect to the alkene to be cyclopropanated.

8. A process according to claim 5, in which 10-20 molar equivalents of dibromomethane is used.

9. A process according to claim 1 in which excess dibromomethane is recovered for further use.

10. A process according to claim 9, in which the recovery is carried out by the steps of:
    (i) adding the reaction mixture to aqueous base at a temperature from −10°-0° C.;
    (ii) warming slowly the resulting two-phase mixture to room temperature;
    (iii) separating the phases;
    (iv) adding isopropanol to the organic phase; and
    (v) drying azeotropically and evaporating the dibromomethane under reduced pressure.

11. A method of manufacturing a flavour or fragrance ingredient, comprising the cyclopropanation of an alkene by a process according to claim 1.

12. A process according to claim 3, in which there is used from 2.5-3.5 molar equivalents, of tri-(C$_2$-C$_8$)-alkyl aluminium reagent.

13. A process according to claim 4, in which there is used from 25-35 molar equivalents, of dibromomethane.

14. A process according to claim 5, in which the metal compound is a Lewis acid selected from FeCl$_2$ and FeCl$_3$.

15. A process according to claim 7 in which the metal compound is used at a concentration of 1-10%, with respect to the alkene to be cyclopropanated.

* * * * *